United States Patent
Kraft et al.

(10) Patent No.: US 10,328,209 B2
(45) Date of Patent: Jun. 25, 2019

(54) ASSEMBLY FOR A DRUG DELIVERY DEVICE AND DRUG DELIVERY DEVICE

(71) Applicant: Sanofi-Aventis Deutschland GMBH, Frankfurt am Main (DE)

(72) Inventors: Torsten Kraft, Frankfurt am Main (DE); Markus Oschmann, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/029,327

(22) PCT Filed: Nov. 10, 2014

(86) PCT No.: PCT/EP2014/074146
§ 371 (c)(1),
(2) Date: Apr. 14, 2016

(87) PCT Pub. No.: WO2015/071211
PCT Pub. Date: May 21, 2015

(65) Prior Publication Data
US 2016/0271331 A1    Sep. 22, 2016

(30) Foreign Application Priority Data

Nov. 15, 2013 (EP) .................................... 13193023

(51) Int. Cl.
*A61M 5/00* (2006.01)
*A61M 5/315* (2006.01)

(52) U.S. Cl.
CPC ...... *A61M 5/31528* (2013.01); *A61M 5/3155* (2013.01); *A61M 5/31551* (2013.01); *A61M 5/31585* (2013.01); *A61M 5/31553* (2013.01)

(58) Field of Classification Search
CPC ..................... A61M 5/31523–5/31595; A61M 5/20–2005/2093; A61M 5/3287; A61M 5/315–2005/31523; A61M 5/24–5/288
(Continued)

(56) References Cited

U.S. PATENT DOCUMENTS

| 3,335,722 A | 8/1967 | Lowry et al. |
| 4,973,318 A | 11/1990 | Holm et al. |
| 2015/0151053 A1* | 6/2015 | Holmqvist ............... A61M 5/24 604/208 |

FOREIGN PATENT DOCUMENTS

| EP | 0688571 | 12/1995 |
| EP | 1603611 | 5/2008 |

(Continued)

OTHER PUBLICATIONS

International Preliminary Report on Patentability in International Application No. PCT/EP2014/074146, dated May 17, 2016, 8 pages.

(Continued)

*Primary Examiner* — Jason E Flick
(74) *Attorney, Agent, or Firm* — Fish & Richardson P.C.

(57) ABSTRACT

An assembly (100) for a drug delivery device is presented. The assembly comprises a housing (10) with a main axis (X), a dose setting member (2) being rotatable with respect to the housing (10) for setting a dose of a drug, an activation member (1) being axially movable with respect to the housing (10) for dispensing the dose from the drug delivery device, and a rotation member (5) being arranged between the activation member (1) and the dose setting member (2). The assembly (100) is configured such that the rotation member (5) is rotatable with respect to the dose setting member (2) and the activation member (1), wherein the (Continued)

outer surface (21) of the assembly (100) comprises the outer surface (22) of the rotation member (5).

12 Claims, 2 Drawing Sheets

(58) Field of Classification Search
USPC .......................................................... 604/211
See application file for complete search history.

(56) References Cited

FOREIGN PATENT DOCUMENTS

| WO | WO 98/56436 | 12/1998 |
|----|-------------|---------|
| WO | WO 99/38554 | 8/1999 |
| WO | WO 2011/039163 | 4/2011 |

OTHER PUBLICATIONS

International Search Report and Written Opinion in International Application No. PCT/EP2014/074146, dated Feb. 18, 2015, 14 pages.

* cited by examiner

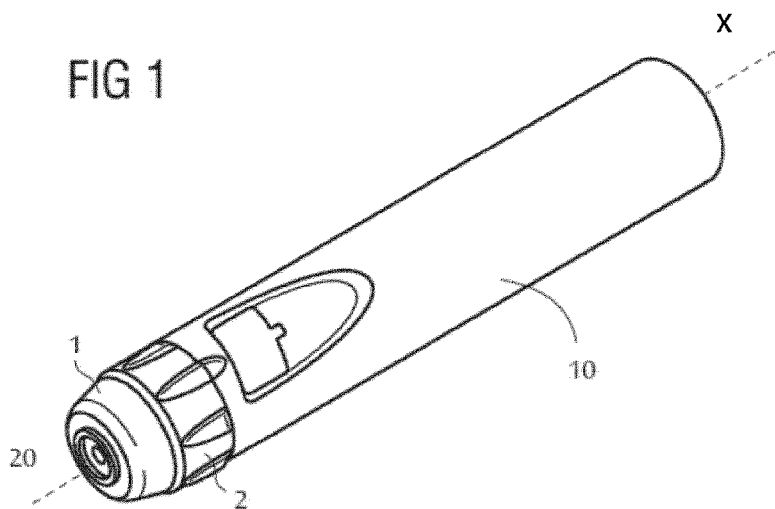
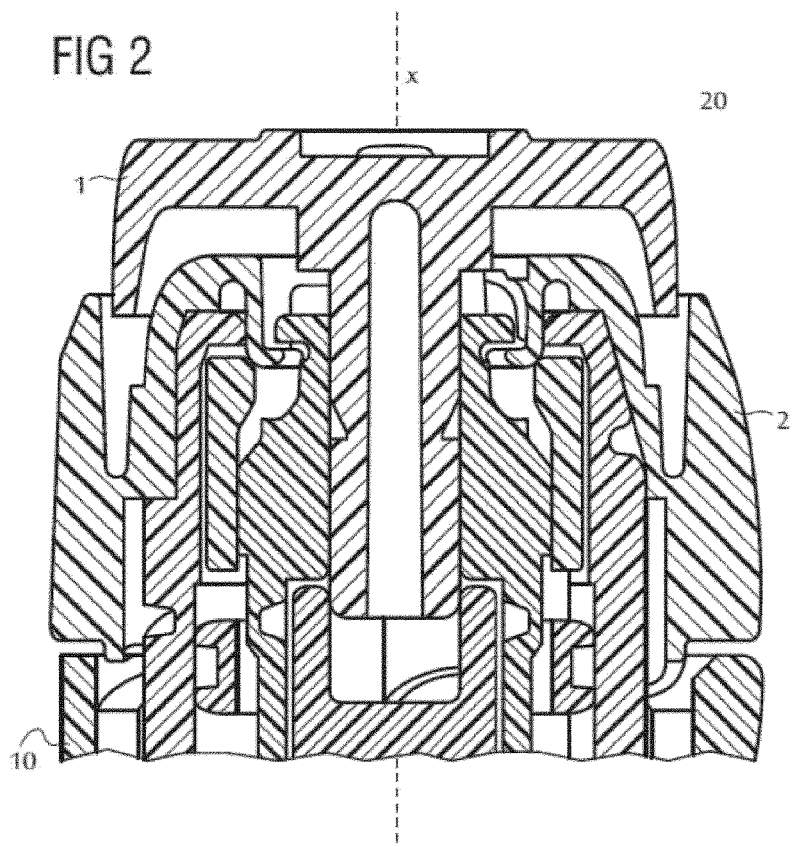

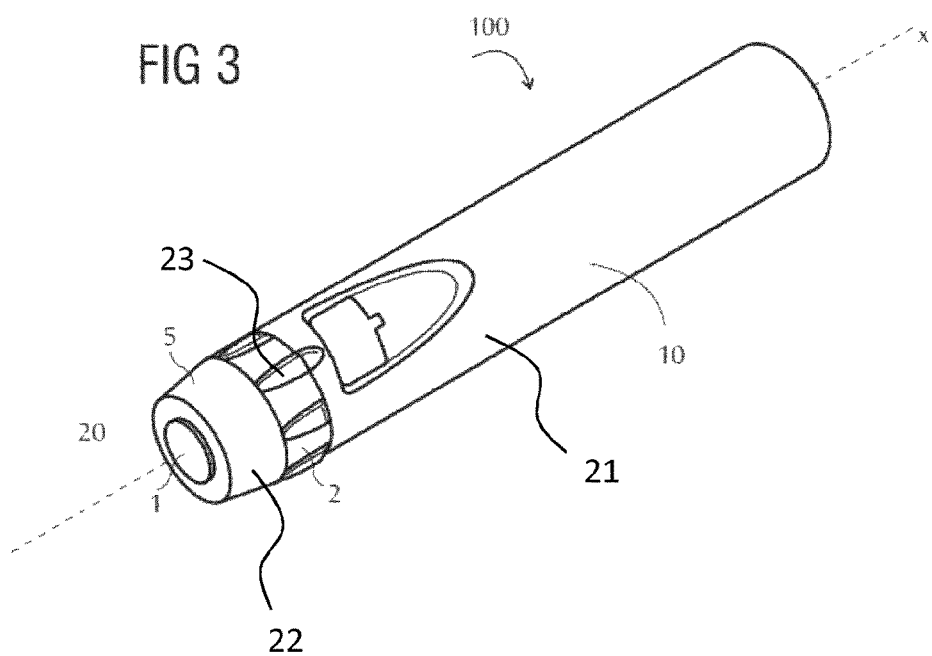
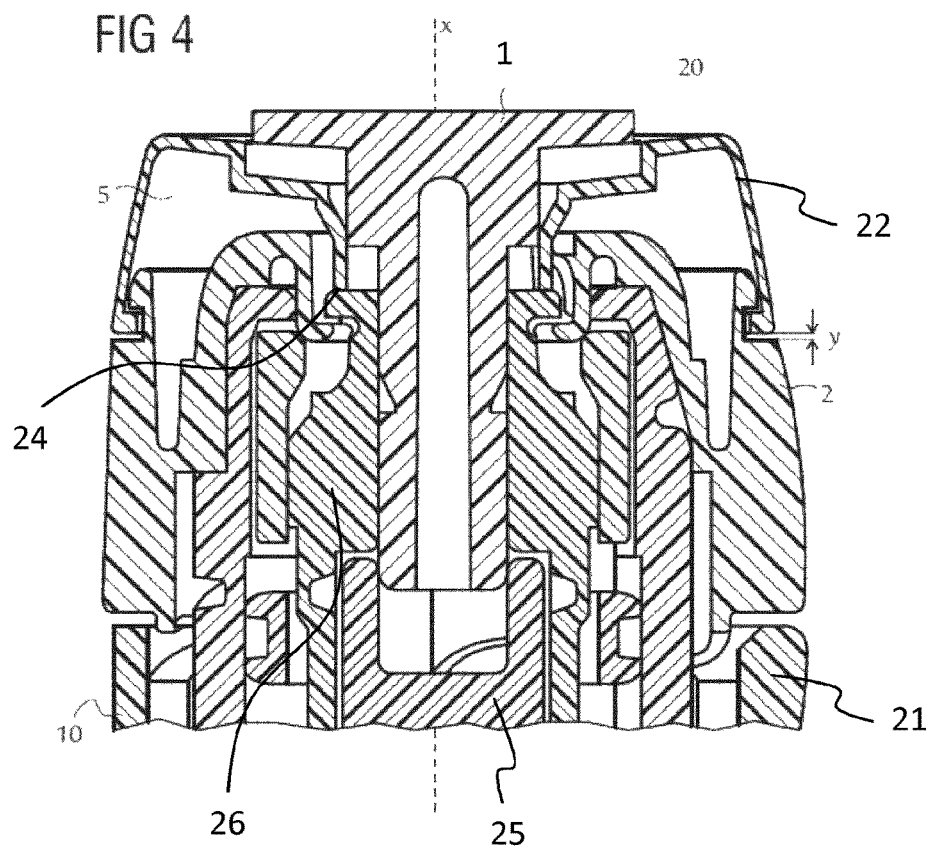

ASSEMBLY FOR A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2014/074146, filed on Nov. 10, 2014, which claims priority to European Patent Application No. 13193023.2, filed on Nov. 15, 2013, the entire contents of which are incorporated herein by reference.

The present disclosure relates to an assembly for a drug delivery device such as an injector-type device and a drug delivery device.

Certain aspects of the present disclosure can be implemented to provide an assembly by which a drug delivery device can be improved. Particularly, the drug delivery device can be rendered more robust and user-friendly when the assembly is applied to the device.

Certain aspects of the present disclosure can be implemented by the subject-matter of the independent claim 1. Advantageous embodiments and refinements are subject-matter of the dependent claims.

One aspect of the present disclosure relates to an assembly for a drug delivery device comprising a housing with a main axis. The main axis may be a longitudinal axis of the housing. The assembly further comprises a dose setting member being rotatable with respect to the housing for setting a dose of a drug. Preferably, the dose setting member is configured such that it can be manually rotated e.g. by a user of the assembly or the drug delivery device for setting of the dose. The assembly further comprises an activation member being axially moveable with respect to the housing for dispensing the dose from the drug delivery device. The activation member may be an activation button, preferably, being configured such that the user may e.g. press or axially move the activation member with respect to the housing for dispensing of the dose.

The assembly further comprises a rotation member being arranged between the activation member and the dose setting member. The rotation member may comprise a ring-like shape. Preferably, the rotation member is axially arranged between the activation member and the dose setting member. The assembly is further configured such that the rotation member is rotatable with respect to the dose setting member and with respect to the activation member, wherein the outer surface of the assembly comprises the outer surface of the rotation member. The assembly and/or the rotation member may, particularly, improve the usability or operability of the assembly or the drug delivery device, particularly for disabled users or patients with limited manual dexterity.

In conventional drug delivery devices, users with short fingers and/or physical disabilities may tend or be obliged to press an activation button in order to dispense a dose of drug. As said device may have a larger longitudinal extension when a dose of drug is set as compared to a state of the device wherein no dose is set, for example, the dispensing button may only be pressed non-centrically or not completely. As the device may have to be gripped by the palm of the user, said extension—at the time of dispensing—may require the user to stretch the thumb in order to be able to press the activation button. When the mentioned enlargement of the extension exceeds a certain extension of the user's thumb, the user is only able to press the activation button at its edges. Then, a dose setting member which may be arranged close to the activation member and rotate during the dispensing of the drug with respect to the activation member may be pressed by the thumb of the user along with the activation button. Thereby, said rotation, such as counter-clockwise rotation, may be blocked and the dispensing may be prevented due to the friction or contact with the user's thumb. If the user, nevertheless, keeps pressing, excessive longitudinal load or force may be applied to the inner mechanics of the device. During a previous setting of a dose of drug, the user may further accidentally or inadvertently press the activation member along with a manipulation of the dose setting member. This may lead to an unwanted dispensing operation and/or to excessive force or distortion applied to inner components, e.g. components of a drive mechanism of the device, especially when a needle has falsely been mounted to the device, not yet been mounted at all or when said needle is blocked. The mentioned force or distortion may lead to damage or destruction of the device.

As an advantage of the presented assembly or device, torque, tangential or longitudinal force exerted on the dose setting member and/or the activation member may be prevented from being transferred to further components by the provision of the rotation member, as said torque or force may be redirected or bypassed by the provision of the rotation member. This may, in turn, prevent distortion of inner components of the assembly or the drug delivery device, particularly during dose setting and/or dose dispensing.

Moreover, it may be prevented that the activation button is pressed accidentally and that, thereby, doses of drug are dispensed inadvertently, especially in case of a blocked needle of the assembly or the drug delivery device. Accordingly, safety of the assembly or the drug delivery device may be increased.

With the presented concept, it may further be prevented that the user of the assembly touches or manipulates the activation member and the dose setting member at the same time.

A further aspect of the present disclosure relates to a drug delivery device comprising the assembly. The drug delivery device may comprise or be connectable to a cartridge comprising the drug. The drug delivery device may further comprise or be connectable to an injection needle through which the drug may be dispensed. Moreover, the drug delivery device may comprise a dose setting mechanism and a drive mechanism.

In an embodiment, the dose setting member is coupled to a dose setting mechanism of the drug delivery device.

In an embodiment the activation member is coupled to a drive mechanism of the drug delivery device.

In an embodiment, the rotation member is freely rotatable around the main axis, e.g. with respect to the housing. Preferably, the rotation member is freely rotatable with respect to any other component of the assembly or the drug delivery device. According to this embodiment, the transfer or exertion of force to/on further components of the assembly or the device, such as a drive mechanism or a dose setting mechanism, may be prevented, particularly during an operation of the assembly. When, for instance, the rotation member is rotated by the user with respect to the housing, said rotation has, preferably, no effect on the functionality of the assembly or the drug delivery device at all. In other words, the rotation member may be configured to rotationally float or slide with respect to further components of the assembly.

An operation of the assembly or the device may relate to a dose setting or a dose dispensing operation.

In an embodiment, the rotation member is arranged directly between the activation member and the dose setting member. According to this embodiment, the rotation member may be arranged such that it separates the dose setting member and the activation member in that the rotation member keeps the dose setting member and the activation member spaced from one another. This may particularly prevent a user from touching or operating the activation member and the dose setting member at the same time.

In an embodiment, the activation member is axially moveable with respect to the rotation member. According to this embodiment, the rotation member may act as a stop face, e.g. for the thumb of the user during pressing or moving the dispensing button for dispensing a dose of drug.

In an embodiment, the diameter of the activation button is less than the diameter of the rotation member.

In an embodiment, the rotation member is disposed to circumferentially surround the activation member.

The previous two embodiments allow a user who e.g. falsely presses the activation button to dispense a dose of drug, will, at a certain point, touch or abut the rotation member with his finger such that an interaction of the user's finger with the dose setting member is likely prevented and therewith an exertion of extensive force on inner components of the assembly and/or the device.

In an embodiment, the activation member extends through the rotation member. This embodiment facilitates specific arrangements of the rotation member, the dose setting member and the activation member of the previous embodiments, wherein, at the same time, an activation of the dose setting mechanism and/or the drive mechanism of the assembly or the drug delivery device is enabled.

In an embodiment, the diameter of the rotation member approximately matches the diameter of the dose setting member. According to this embodiment, it may be achieved that a user intending to set or dial the dose of drug by rotation of the dose setting member with respect to the housing may at the same time touch the rotation member which may then also rotate with respect to the housing. Said rotation of the rotation member or the mere existence of the rotation member may, advantageously, prevent the user from touching or interacting with the activation button such that, during setting of a dose, neither a dose of drug is dispensed inadvertently nor any unwanted or destructing force or torque is exerted on inner components of the assembly or the drug delivery device.

In an embodiment, the activation member is arranged at a proximal end of the assembly. The "proximal end" of the assembly or the drug delivery device or a component thereof shall mean the end which is furthest away from a dispensing end of the drug delivery device. The "distal end" of the assembly or the drug delivery device or a component thereof may mean the end which is closest to the dispensing end of the drug delivery device. According to this embodiment, the operation of the assembly of the drug delivery device may be achieved easiest and most expediently.

The term "drug", as used herein, preferably means a pharmaceutical formulation containing at least one pharmaceutically active compound, wherein, in one embodiment, the pharmaceutically active compound has a molecular weight up to 1500 Da and/or is a peptide, a protein, a polysaccharide, a vaccine, a DNA, an RNA, an enzyme, an antibody or a fragment thereof, a hormone or an oligonucleotide, or a mixture of the above-mentioned pharmaceutically active compounds, wherein, in a further embodiment, the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein, in a further embodiment, the pharmaceutically active compound comprises at least one peptide for the treatment and/or prophylaxis of diabetes mellitus or complications associated with diabetes mellitus such as diabetic retinopathy, wherein, in a further embodiment, the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl- ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivatives.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and E have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features which are described herein above and below in conjunction with different aspects or embodiments may also apply to other aspects and embodiments. Further features and advantageous embodiments of the subject matter of the disclosure will become apparent from the following description of the exemplary embodiment in conjunction with the figures, in which:

FIG. 1 shows a perspective view of an assembly.

FIG. 2 shows a longitudinal section of a portion of the assembly shown in FIG. 1.

FIG. 3 shows a perspective view of an assembly 1 according to an embodiment of the present disclosure.

FIG. 4 shows a longitudinal section of a portion of the assembly shown in FIG. 3.

Like elements, elements of the same kind and identically acting elements may be provided with the same reference numerals in the figures. Additionally, the figures may be not true to scale. Rather, certain features may be depicted in an exaggerated fashion for better illustration of important principles.

FIG. 1 shows an assembly or a drug delivery device. The assembly comprises a housing 10 with a longitudinal axis X. The assembly further comprises a dose setting member 2. The assembly further comprises an activation member 1. The activation member 1 is arranged at a proximal end 20 of the assembly. The activation member 1 is an activation button. The dose setting member 2 is arranged near the proximal end 20. The dose setting member 2 is furthermore rotatable with respect to the housing 10 in order to set or dial a dose of drug to be dispensed from a drug delivery device. The activation member 1 is axially moveable with respect to the housing 10, at least within certain limits, in order to dispense a dose of drug from the assembly or the drug delivery device.

FIG. 2 shows a longitudinal section of at least a portion of the assembly shown in FIG. 1. In the depicted situation, the assembly is, preferably, in a dose setting state, in which a dose of drug may be set. In this state, the activation member 1 can still be pressed with respect to the housing 10 and/or with respect to the dose setting member 2 in order to dispense the set dose. Preferably, the dose setting member 2 is axially constrained with respect to the housing 10. It is further apparent that the assembly comprises further inner components (not explicitly indicated), e.g. of a drive mechanism to which the activation member 1 is coupled in order to dispense a dose of drug from the assembly or the device.

FIG. 3 shows a perspective view of an assembly 100 according to an embodiment of the present disclosure. The assembly 100 is, preferably, applied in the drug delivery device which is not explicitly indicated in the Figures of the present disclosure. The assembly 100 may constitute the drug delivery device. The dose setting member 2 is, preferably, coupled to a dose setting mechanism of the assembly or of the drug delivery device. The activation member 1, on the other hand, is, preferably, coupled to a drive mechanism of the assembly 100 or, as the case may be, of the drug delivery device.

In contrast to the assembly shown in FIG. 1, the assembly of FIG. 3 further comprises a rotation member 5. The rotation member 5 is arranged or retained between the activation member 1 and the dose setting member 2. The outer surface 21 of the assembly 100 comprises the outer surface 22 of the rotation member 5. In other words, the outer surface 21 of the assembly 100 and the outer surface 22 of the rotation member 5 may be flush. Moreover, the rotation member 5 is slidable and/or rotatable around the longitudinal axis X with respect to the dose setting member 2 and the activation member 1 and, preferably, also with respect to the housing 10. To this effect, the rotation member 5 may be a gliding member. Moreover, the dose setting member 2 and rotation member 5 are configured sleeve-like.

The rotation member 5 is arranged directly between the activation member 1 and the dose setting member 2. The rotation member 5 is configured ring-like. The rotation member 5 is further disposed to circumferentially surround the activation member 1. The activation member 1, preferably, extends through the rotation member 5 (cf. also FIG. 4). The activation member 1 may further at least partly extend through the dose setting member 2. The diameter of the activation member 1 is smaller than the diameter of the rotation member 5. The diameter of the rotation member 5 approximately matches the diameter of the dose setting member 2. The rotation member 5 may further be tapered slightly towards the proximal end 20, as depicted in FIG. 3 in order to improve handiness of the assembly 100 and/or the device. The rotation member 5 is, furthermore freely, i.e. with a low frictional resistance, rotatable with respect to the dose setting member 2 and with respect to the activation member 1. Preferably, the rotation member 5 is also rotatable with respect to the housing 10. As an advantage of said free rotation, torque, tangential and/or longitudinal force exerted on the dose setting member 2 and/or the activation member 1 may be prevented from being transferred to the drive mechanism of the assembly or the device, for example.

Said torque or force may be prevented in that it is redirected or bypassed by the free rotation of the rotation member 5. This may, in turn, prevent distortion of inner components (see below) of the drive mechanism, particularly during dose setting and/or dose dispensing. Moreover, it may be prevented that the activation button 1 is pressed accidentally and that, thereby, doses of drug are dispensed inadvertently, especially in the case of a blocked needle (not depicted) of the assembly 100 or the drug delivery device. The provision of the rotation member 5 may allow for a load rejection of the inner mechanics of the assembly 100 and/or the device.

The rotation member may further be axially secured with respect to the housing 10.

The dose setting member further comprises gripping features 23 which may facilitate a dose setting operation which is performed manually by the user in that the user rotates the dose setting member 2 with respect to the housing 10.

FIG. 4 shows a longitudinal section of at least a portion of the assembly 100 shown in FIG. 3. In the depicted situation, the assembly 100 is, preferably, in a dose setting state, in which the activation member 1 can still be pressed with respect to the housing 10 and/or with respect to the dose setting member 2 in order to dispense a set dose, as explained above. Preferably, the dose setting member 2 is axially constrained with respect to the housing 10. It is further apparent that the arrangement of the rotation member 5 comprises or allows for a certain play or play distance Y of the rotation member 5. This further enables a mechanical load rejection from the inner components e.g. of the assembly or the drive mechanism. The assembly 100 or the device further comprises a drive sleeve 26 and a piston rod 25 which may be arranged inside of the drive sleeve and configured to be driven or moved by the drive sleeve 26. Preferably, the piston rod 25 extends at least partly through the drive sleeve 26. It is further shown that the rotation member 5 comprises an abutment face 24 abutting a proximal face (not explicitly indicated of the drive sleeve 26.

When the desired dose has been dialled or set, as described above, the user may then dispense this dose by depressing or axially moving the activation member 1 with respect to the housing 10 along the longitudinal axis X. To this effect, the assembly 100 may be configured such that the movement of the activation member may cause the drive sleeve 26 of the assembly 100 or the device to drive the piston rod 25 of the assembly 100 or the device distally, such that a piston (not explicitly indicated) may be advanced in a cartridge to dispense the set dose.

With regard to the functioning principle of the above-mentioned dose setting or dose dispensing or drive mechanism of the device, is referred to the document EP 1603611 B1 which is herein incorporated by reference.

The scope of protection is not limited to the examples given herein above. The invention is embodied in each novel characteristic and each combination of characteristics, which particularly includes every combination of any features which are stated in the claims, even if this feature or this combination of features is not explicitly stated in the claims or in the examples.

REFERENCE NUMERALS

1 Activation member
2 Dose setting member
5 Rotation member
10 Housing
20 Proximal end
21 Outer surface (assembly)
22 Outer surface (rotation member)
23 Gripping feature
24 Abutment face
25 Drive sleeve
26 Piston rod
100 Assembly
X Longitudinal axis
Y Distance

The invention claimed is:

1. An assembly for a drug delivery device, the assembly comprising:
   a housing comprising a main axis;
   a dose setting member being rotatable with respect to the housing for setting a dose of a drug;
   an activation member being axially movable with respect to the housing for dispensing the dose from the drug delivery device; and
   a rotation member being arranged between the activation member and the dose setting member, wherein the rotation member is disposed circumferentially surrounding the activation member, wherein the rotation member is rotatable with respect to the dose setting member and the activation member, wherein the rotation member is configured to rotate or axially translate independently from the dose setting member and the activation member, wherein an outer surface of the assembly comprises an outer surface of the rotation member.

2. The assembly according to claim 1, wherein the rotation member is freely rotatable around the main axis.

3. The assembly according to claim 1, wherein the rotation member is arranged directly between the activation member and the dose setting member.

4. The assembly according to claim 1, wherein the activation member is axially movable with respect to the rotation member.

5. The assembly according to claim 1, wherein a diameter of the activation member is smaller than a diameter of the rotation member.

6. The assembly according to claim 1, wherein a diameter of the rotation member substantially matches a diameter of the dose setting member.

7. The assembly according to claim 1, wherein the activation member is arranged at a proximal end of the assembly.

8. The assembly according to claim 1, wherein the dose setting member is configured sleeve-like.

9. The assembly according to claim 1, wherein the activation member is an activation button.

10. A drug delivery device comprising:
   an assembly comprising:
      a housing comprising a main axis;
      a dose setting member being rotatable with respect to the housing for setting a dose of a drug;
      an activation member being axially movable with respect to the housing for dispensing the dose from the drug delivery device; and
      a rotation member being arranged between the activation member and the dose setting member, wherein a diameter of the activation member is smaller than a diameter of the rotation member, wherein the rotation member is rotatable with respect to the dose setting member and the activation member, wherein the rotation member is configured to rotate or axially translate independently from the dose setting member and the activation member, wherein an outer surface of the assembly comprises an outer surface of the rotation member.

11. The drug delivery device of claim 10, further comprising a drug carried in the housing.

12. The drug delivery device of claim 11, wherein the drug comprises a pharmaceutically active compound.

* * * * *